US006588426B2

(12) United States Patent
Linderoth

(10) Patent No.: US 6,588,426 B2
(45) Date of Patent: Jul. 8, 2003

(54) TRACHEOSTOMY SAFETY DEVICE

(76) Inventor: Craig D. Linderoth, 16639 Mindota Ave., Norwalk, WI (US) 54648

( * ) Notice: Subject to any disclaimer, the term of this patent is extended or adjusted under 35 U.S.C. 154(b) by 0 days.

(21) Appl. No.: 09/935,434

(22) Filed: Aug. 23, 2001

(65) Prior Publication Data

US 2002/0029782 A1 Mar. 14, 2002

Related U.S. Application Data

(60) Provisional application No. 60/229,622, filed on Aug. 31, 2000.

(51) Int. Cl.[7] .............................................. A61M 16/00
(52) U.S. Cl. ............................ 128/207.14; 128/200.26; 128/202.27; 285/80
(58) Field of Search ........................ 128/207.14, 207.15, 128/207.29, 200.26, DIG. 26, 202.27; 285/80, 81, 86, 305, 321

(56) References Cited

U.S. PATENT DOCUMENTS

| 2,908,269 | A | * | 10/1959 | Cheng .......................... 600/237 |
|---|---|---|---|---|
| 3,760,811 | A | * | 9/1973 | Andrew .................. 128/207.17 |
| 4,249,529 | A | * | 2/1981 | Nestor et al. ........... 128/207.17 |
| 4,315,505 | A | * | 2/1982 | Crandall et al. ........ 128/200.26 |
| 4,774,944 | A | * | 10/1988 | Mischinski ............. 128/207.17 |
| 4,832,019 | A |   | 5/1989 | Weinstein et al. ...... 128/207.17 |
| 4,906,234 | A |   | 3/1990 | Voychehovski ............... 604/79 |
| 5,026,352 | A |   | 6/1991 | Anderson .................... 604/178 |
| 5,067,496 | A |   | 11/1991 | Eisele ..................... 128/207.15 |
| 5,069,206 | A |   | 12/1991 | Crosbie ................... 128/207.17 |
| 5,076,269 | A |   | 12/1991 | Austin .................... 128/207.17 |
| 5,320,097 | A |   | 6/1994 | Clemens et al. ........ 128/207.17 |
| 5,330,235 | A |   | 7/1994 | Wagner et al. ................. 285/81 |
| 5,345,931 | A |   | 9/1994 | Battaglia, Jr. .......... 128/207.17 |
| 5,437,273 | A |   | 8/1995 | Bates et al. ............. 128/207.17 |
| 5,437,483 | A |   | 8/1995 | Umezawa .................... 285/308 |
| 5,460,176 | A |   | 10/1995 | Frigger ................... 128/207.14 |
| 5,551,421 | A |   | 9/1996 | Noureldin et al. ...... 128/207.17 |
| 5,653,232 | A | * | 8/1997 | Rogers et al. .......... 128/207.17 |
| 5,803,079 | A | * | 9/1998 | Rogers et al. .......... 128/207.14 |
| 5,806,516 | A | * | 9/1998 | Beattie ................... 128/207.17 |
| 5,894,840 | A | * | 4/1999 | King ...................... 128/200.26 |
| 5,934,276 | A | * | 8/1999 | Fabro et al. ............ 128/207.17 |
| 6,009,872 | A | * | 1/2000 | Delaplane et al. ..... 128/207.17 |
| 6,010,484 | A | * | 1/2000 | McCormick et al. ....... 604/174 |
| 6,029,668 | A | * | 2/2000 | Freed ..................... 128/207.17 |
| 6,065,779 | A | * | 5/2000 | Moner et al. ................. 285/23 |
| 6,067,985 | A | * | 5/2000 | Islava .................... 128/207.17 |
| 6,206,885 | B1 | * | 3/2001 | Ghahremani et al. ......... 606/96 |
| 6,361,523 | B1 | * | 3/2002 | Bierman ..................... 604/174 |
| 6,408,850 | B1 | * | 6/2002 | Sudge ................... 128/207.17 |

FOREIGN PATENT DOCUMENTS

GB 2077377 * 12/1991

OTHER PUBLICATIONS

No preliminary patentability search was conducted. The Shiley Disposable Inner Cannula low pressure cuffed tracheostomy device manufactured and distributed by Mallinckrodt, Inc., St. Louis, MO 63134, is a known medical device for which the applicant is not aware of any patents covering the device. The attached copy of the disposable inner cannula with 15 mm snap–lock connector appears on the backside information panel of a blister package. The drawings of the captioned application depict the device and show the improvements to the device.

* cited by examiner

Primary Examiner—Weilun Lo
Assistant Examiner—Mital Patel
(74) Attorney, Agent, or Firm—M. Paul Hendrickson

(57) ABSTRACT

Unwanted separation of an inner cannula from an outer cannula in tracheostomy devices can be achieved by installing a retaining ring which prevents the inner cannula from unwantingly being unlatched from the outer cannula. The retaining ring allows the air supply elbow to be separated which, in turn, permits the sensory alarms to properly sound when a disconnection of the air supply arises.

8 Claims, 7 Drawing Sheets

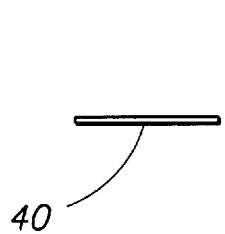
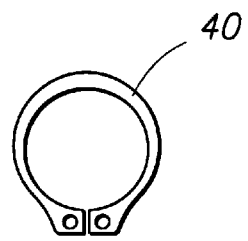
FIG. 6A          FIG. 6B
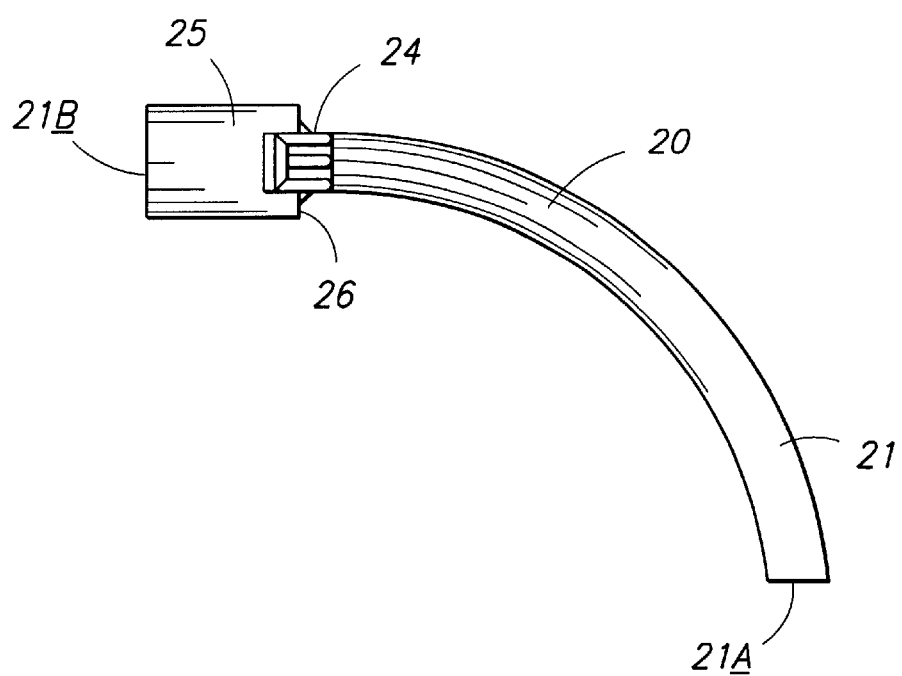
FIG. 7

TRACHEOSTOMY SAFETY DEVICE

This non-provisional application claims the benefits of provisional application Serial No. 60/229,622 entitled the same and filed Aug. 31, 2000 on behalf of Craig D. Linderoth.

FIELD OF INVENTION

The present invention relates to a medical safety device and, more particularly, to a tracheostomy safety device and its use.

BACKGROUND OF THE INVENTION

Tracheostomy devices are extensively used within the medical field to ventilate or assist patients with respiratory problems. Many patients with advanced stages of gas exchange impairment (e.g. COPD, multiple sclerosis, emphysema, etc.) are dependent upon effective utilization of the tracheostomy devices to supply oxygen and discharge exhaled gases from the respiratory system. Any inadvertent or unwanted cessation of the respiratory exchange by the tracheostomy devices within the medical unit can lead to irreparable injury or death of the patient.

The ventilator units are usually equipped with sensory or alarm systems designed to detect certain abnormalities such as gas pressure loses within the device. Typically a sudden operational decrease in back pressure activates a remote alarm system so as to alert the medical staffing so that the device may be restored to a life sustaining operation.

One of the most popular tracheostomy devices is a device referred to as a Shiley disposal cannula low pressure cuffed tracheostomy device manufactured and distributed by Mallinokrodt, Inc. (St. Louis, Mo. 63134) fitted with a rigid neck plate and what is referred to as a STRONGHOLD retainer for harnessing the tracheostomy device so that the inner cannula cannot be inadvertently separated from the outer cannula.

The SHLEY device includes an inner cannula and an outer cannula operatively connected to an oxygen or air supply and a low pressure sensory for the alarm system. The outer cannula includes a larger tubular section with an inflatable cuff encompassing a distal end section of the tube and a notched flanged rim at a proximate tube end with a flared seating collar for connecting to the inner cannula. The inner cannula comprises a tubular passageway fitted with a projecting tubular portion and a collared seat for seating and sealing onto the flanged collar of the outer cannula. The projecting tubular portion of the inner cannula is sized to concentrically fit within the outer cannula passageway. The inner cannula functions as an air passageway for ventilating the patient. An enlarged hollow cylindrical extension capped with a brim which anchors the stem of the projecting tubular portion completes the air pathway of the inner cannula. The enlarged tubular air line cylindrical extension having a larger external diameter than the outer diameter of the outer cannula serves as a connecting site for a ventilator connecting elbow which connects the ventilator gas supply lines to the tracheostomy device.

The cylindrical extension also serves as a mounting site for mounting the outer cannula onto the inner cannula. The brim of the cylindrical extension includes a pair of aligning ledges which mate onto notched sections of the notched rim. The extension has the appearance of a hollow cylindrical member with the tubular section spouting outwardly from the stem of the opposite end. The cylindrical member serves as a connecting site for a connecting elbow for the air supply lines.

The cylindrical extension includes a flared seat on the latching side which sealingly fits against flared collar of the outer cannula. A pair of jutting ledges extending outwardly from the top edge of brim of the cylindrical extension of the inner cannula serves as a support for the latching assembly. The cylindrical member is equipped with a pair of latching assemblies which latched the outer cannula to the inner cannula. The latching assemblies outwardly extending ledges are laterally positioned at a sufficient outwardly position so as to provide annular clearance for the latches from the outer cannula rim. The undersides of the extending bridges are notched with channeled grooves to impart improved hingeability to the latches.

The latching assemblies of the inner cannula include a pair of flexible latches in the form of extending arms along the outer peripheral margin of the jutting ledges which extend upwardly and inwardly terminated by L-shaped latching tab or claw which engage onto the notched rim of the outer cannula so as to snuggly hold the outer cannula rim onto the inner cannula rim. The arms extend downwardly and outwardly from the ledges to form depressing tabs which, when depressed, place the latches in an unlatched position.

When used, the outer cannula is inserted into the trachea of the patient with the inflatable cuff inflated to seal the outer cannula to the trachea. The inner cannula tube with the connected or unconnected gas supply lines is then inserted onto the outer cannula in a seating position and then latched together with the latches. Normally the harness for the neck plate is secured to the patient to hold the tracheostomy unit in place when ventilation of the patient is commenced. A ventilating elbow connector forms a connecting elbow between the inner cannula and the air lines to the air sources. When the STRONGHOLD anti-disconnect device is used, it straps the elbow connector to the neck plate so as to prevent the elbow connector and the inner cannula from being inadvertently separated from the outer cannula.

Unfortunately, the aforementioned tracheostomy device creates problems for an impaired patient which, if uncorrected, can cause irreparable damage or death to the patient. The ventilating device, with or without the STRONGHOLD, creates serious health risks to patients using the Shiley ventilating device. Without the STRONGHOLD, the latches for latching the inner cannula to outer cannula can become unlatched causing a disruption of the crucial air supply to the patient. Obese patients with excessive neck fat or double chins can unknowingly manipulate the latches with the neck excess sufficiently to unlatch the latching system. This causes a break in the air passageway and a severance of air supply to the patient. Since the inner cannula remains connected to the air source, the sensing system will not detect any appreciable decrease in gas back pressure and, therefore, will not sound the alarm system. Consequently, the medical staffing will be unaware that the patient is in distress and will die if the problem remains uncorrected.

Another particularly serious problem arises in the case of those tracheostomy devices equipped with the STRONGHOLD when the unattended patient becomes restless, startled or panicked by respiratory or ventilating irregularities. Panicky or startled patients will often grasp the connecting elbow of the tracheostomy device with such force so as to pull the entire device, including the inflated cuff, from the trachea causing the ventilating gases to escape into the atmosphere. Since the inner cannula remains connected, there is no detectable back pressure decrease so that the alarm system will not normally detect and sound the alarm under these life-threatening conditions. When an ambulatory patient coughs to clear a plug in the throat, the startled patient will often unconsciously grasp or elbow the device so as to dislodge the entire device, including inflated cuff, from the trachea often causing serious harm or injury to the patient. Thus, the addition of the STRONGHOLD anti-disconnect device does not alleviate those problems associated with the tracheostomy device.

There exists a need to avoid unwanted disconnection of the inner cannula from the outer cannula. There exists a need for an anti-disconnect device which prevents unlatching but yet permits a detectable separation at the connecting elbow. There exists a need for an anti-disconnect device which prevents unwanted unlatching of the inner cannula from the outer cannula and unwanted disengagement of the entire tracheostomy device including the inflated cuff from the patient's trachea. If the latching system could be maintained latched until knowingly unlatched by hospital or medical staffing, patients needlessly suffering of loss of life or serious injury could be avoided. Crucial notice of a failure of a patient's tracheostomy unit by timely sounding of the alarm system would avoid catastrophic injury or death to the user of the device.

SUMMARY OF THE INVENTION

Safety of using a tracheostomy device by preventing unauthorized or undetected separation of the inner cannula from the outer cannula can be achieved by installing a latching stop against the latches so as to prevent unwanted unlatching. An annular retaining ring buttressed against the latches effectively prevents an unlatching movement of the latches and maintains the latches in the latching position. The latch retaining ring is positioned so as to prevent a patient from intentionally or unintentionally removing the latching stop from the unlatching position. This allows only the authorized personnel to remove the latching stop from the latching position. The latch retaining ring prevents only separation or unlatching of the inner cannula from the outer cannula. If separation of ventilating passageway occurs, it occurs at the connecting elbow, thus, preserving the inflated trachea cuff and the alarm system.

The latching stop mechanism allows the low pressure alarming system to perform its intended function of alarming medical personnel in crucial life-threatening situations. Failure of the alarming system to notify medical staffing of an undetectable separation of the inner cannula from the outer cannula is effectively avoided by the inclusion of the latching stop mechanism of this invention.

BRIEF DESCRIPTION OF THE DRAWINGS

FIG. 6A is a side view of the locking attachment used to interlock the outer cannula to the inner cannula as shown in FIGS. 1–3 and 5.

FIG. 6B is a top view of the interlocking attachment shown in FIG. 6A.

FIG. 7 is a side view of the inner cannula shown in FIGS. 1–5.

DETAILED DESCRIPTION OF THE INVENTION

Figure 4:
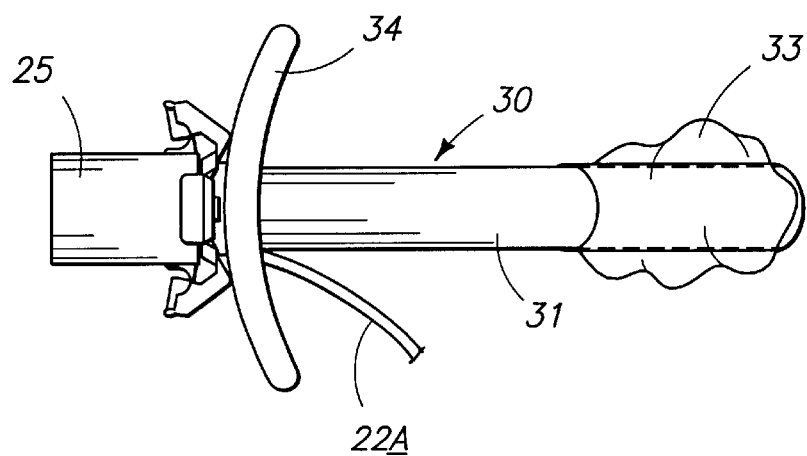
FIG. 4 depicts FIG. 3 without the safety locking attachment.
Figure 5:
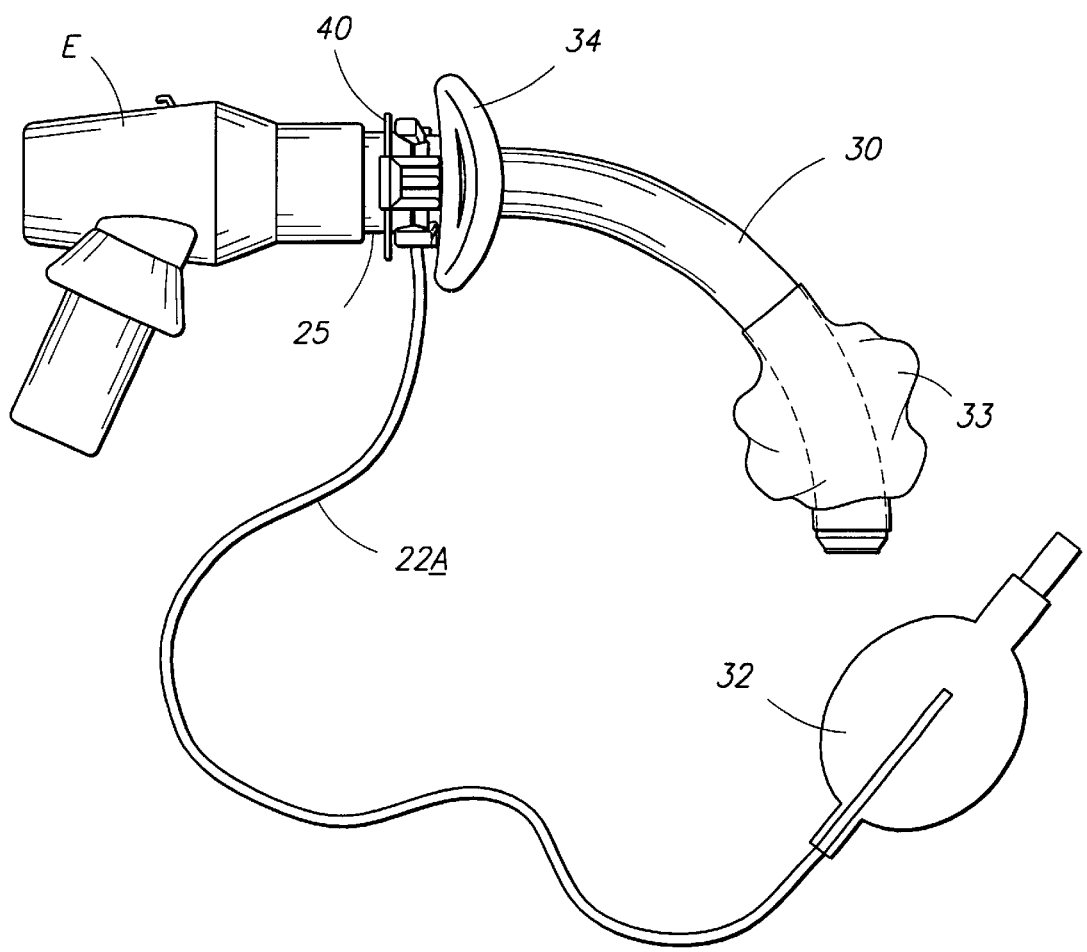
FIG. 5 is a side view of the tracheostomy unit shown in FIG. 1.
Figure 8:
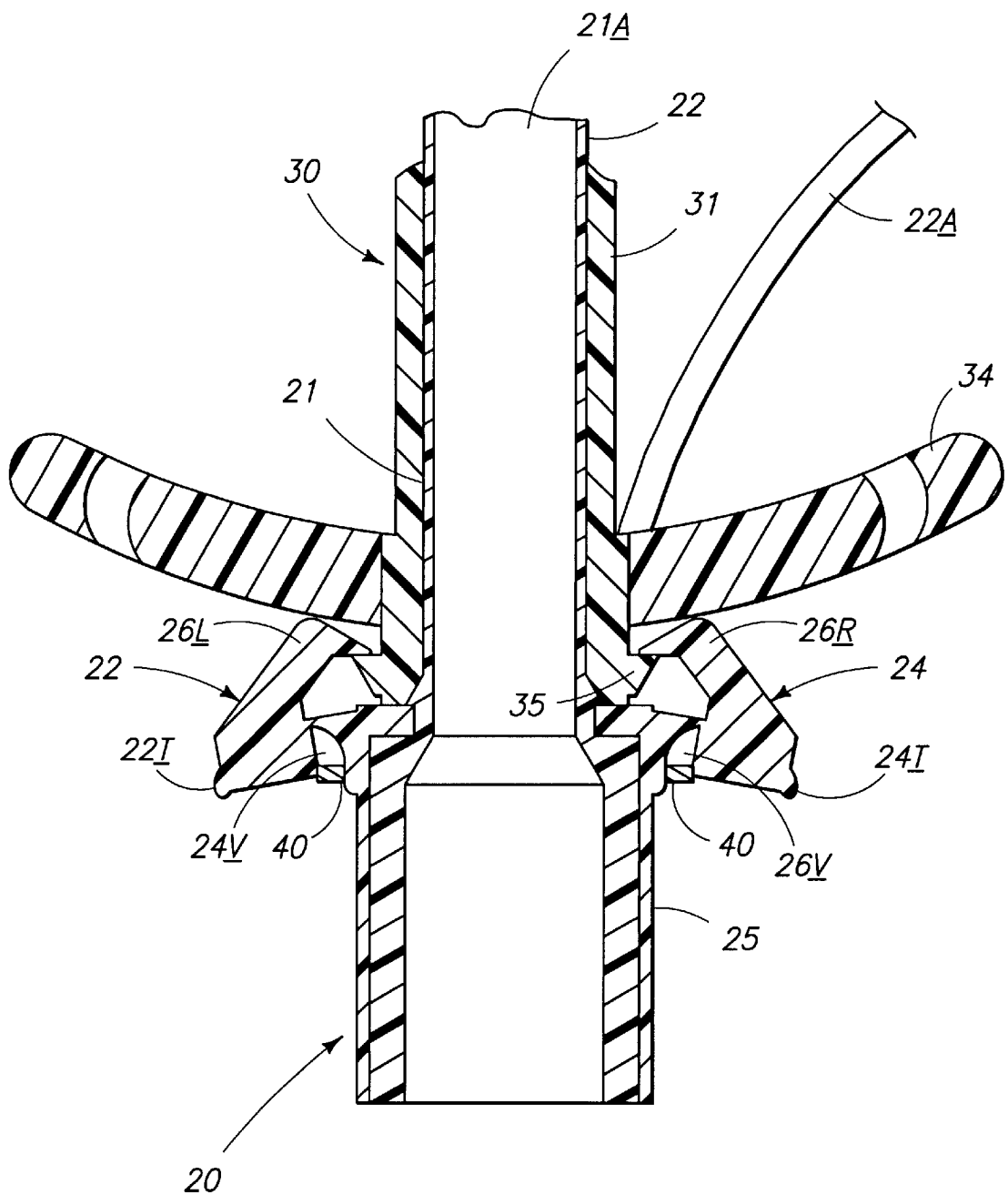
FIG. 8 is a cross-sectional view taken along line 8—8 of FIG. 1.

Pursuant to the present invention, there is provided a tracheostomy device (generally referred as 1) equipped with an interlocking stop (generally referenced as a 40 series number) which prevents an inner cannula 20 from being accidentally separated from an outer cannula 30 without first removing the interlocking stop 40 from the assembled inner 20 and outer 30 cannulas. The tracheostomy device as depicted without the interlocking 40 stop as shown in FIG. 4 is manufactured and distributed by Mallinokrodt, Inc., Critical Care Division, St. Louis, Mo. 63134, in various sizes (e.g., men, women, children, etc.) such as a Shiley adult model fitted with a rigid neck plate 34 and a neck strap 34S which straps the tracheostomy device to the patient's neck. An anti-disconnect accessory identified as STRONGHOLD (not shown) for strapping elbow E to neck plate 34 has heretofore been used to anchor the inner cannula 20 and the outer cannula 30 together and, thereby, prevent unlatching. The present invention incorporates an interlocking stop 40 which avoids inadvertent disconnection of the inner cannula 20 from the outer cannula 30 while allowing the connecting elbow E to separate from the inner cannula 20.

Figure 1:
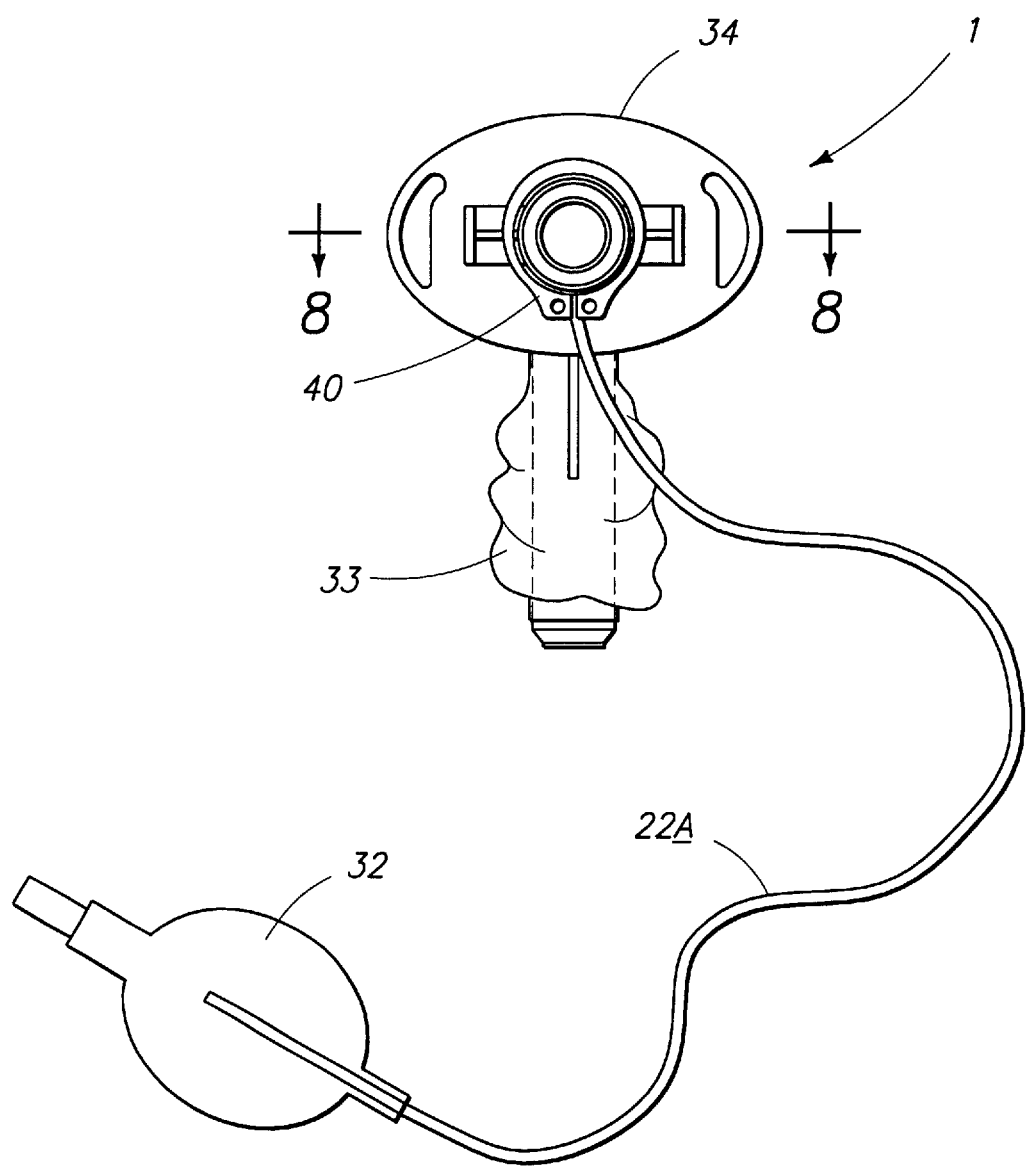
FIG. 1 is a frontal view of an assembled tracheostomy unit equipped with the safety locking embodiments of this invention.
Figure 2:
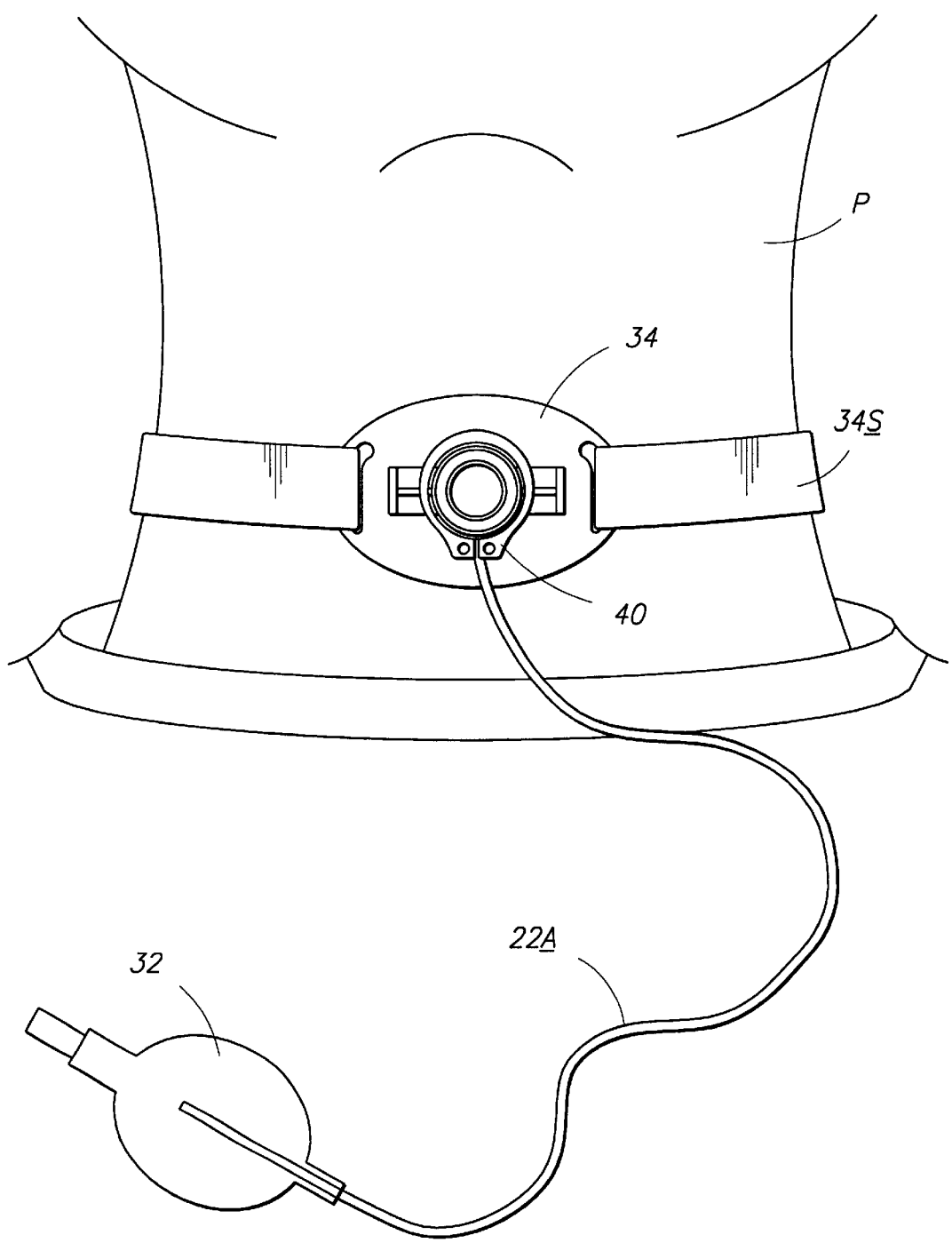
FIG. 2 is a frontal view of the unit shown in FIG. 1 attached to a patient.
Figure 3:
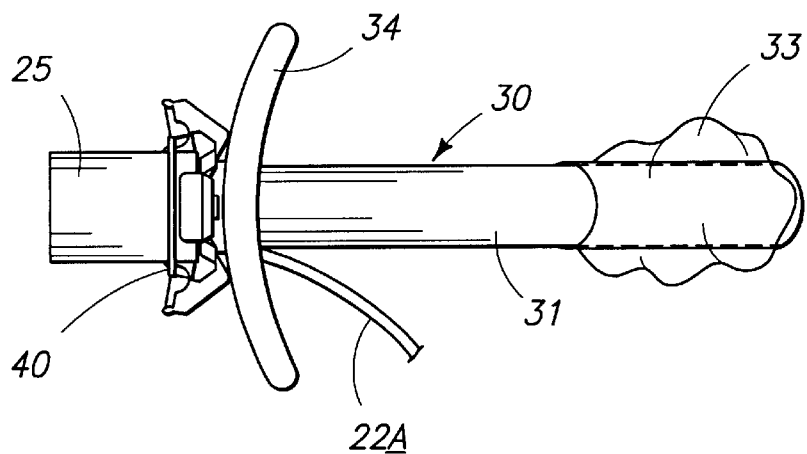
FIG. 3 is a top view showing in part the assembled tracheostomy unit of FIG. 2.

The inner 20 and outer 30 cannulas comprise concentric tubular members adapted to interlock onto one another when the tracheostomy device 1 is assembled for use by a patient. The outer cannula 30 comprises an outer tube 31 fitted with an inflatable cup 33 or bag, which circumscribes the distal end of the outer tubular section cannula 30 and, when inserted in the trachea of a patient P, may be inflated via pumping air pressure bulb 32 to pump air through inflating lines 22A so as to seal the tracheostomy device 1 against the trachea opening of the patient P. The opposite (proximate) end of tube 31 includes a flanged rim 35 equipped with a pair of seating grooves 36 which, as explained later, seat onto mating ledges of latching legs 26L and 26R of the inner cannula 20. A beveled annular flared female seat 38 buttressed against the inward side of rim 35 forms airtight union when drawn snuggly against a mating male flared fitting 28 of the inner cannula 20. An attachable neck rest 34 seated onto the outer cannula tube 31 permits the device 1 to be attached to the patient's neck with drawstrings 34S as illustrated in FIG. 2.

The inner cannula 20 comprises a hollowed cylindrical base 25 and tubular section 21 adapted to sealingly seat within an open passageway 37 of the outer cannula 30. The inner cannula 20 thus includes a smaller diameter tubular section 21 adapted to seat within passageway 37 of the outer cannula 30 and open at both ends so as to provide a passageway 21A for gases from and to the trachea to flow therethrough.

The proximate end of the inner cannula 20 comprises a hollowed cylindrical base 25 equipped with a brim 29 of a larger diameter than the outer cannula tube 31. Brim 29 includes a centrally disposed spouting orifice 23C spouting and connecting tubular section 21 to hollowed base 25 at stem 23. Circumscribing tubular section 21 at stem 23 (the interfacing of base 23 and tubular section 21) is a flared male seat 28 for seating onto a mating female flanged seat 38 of the outer cannula 30. Cylindrical base 25 is hollowed in the center so as to provide an air passageway 21B which interconnects onto air passageway 21A of the inner cannula 20. The cylindrical base 25 supports the inner cannula tube 20. The anterior portion of cylindrical base 25 extends perpendicularly outwardly from the stem 23 of the inner cannula tube 21 to form brim 29 and the interfacing top surface of cylindrical base 25 closure which spouts onto the stem 23 of the inner cannula tube 21A. The interfacing top surface of brim 29 is circular and flat (except for seats 28) so as to rest flushly against outer cannula rim 35 and form a sealed passageway therewith. The perimeter of cylindrical top surface of brim 29 is equipped with a pair of outwardly extending ledges or bridges 22B and 24B which respectively support latching legs 26L and 26R.

The brim 29 of cylindrical base 25 of the inner cannula 20 includes a pair of hinged latches 22 and 24 which latch the inner cannula 20 onto the outer cannula 30. Latches 22 and 24 are positioned about the peripheral margin of brim 29 of inner cylindrical base 25 cannula. Latches 22 and 24 respectively include bridged sections 22B and 24B of molded plastic which interconnect legs 26L and 26R of latches 22 and 24 to the cylindrical base 25 with each of legs 26L and 26R of the latches 22 and 24 including a projecting legged tab 22T and 24T of legs 26L and 26R which extends outwardly and downwardly from hinged bridges 22B and 24B. The underside of bridged regions 22B and 24B include notched grooves 22V and 24V which impart hingeability and flexibility to latches 22 and 24. Notched grooves 24V and 26V also serve as a nesting channel for retaining stop ring 40 so as to prevent hinging and downward depression of tabs 22T and 24T. The terminating end of each latching member 22 and 24 is equipped with a latching hook 22H and 24H adapted to engage onto lip 35L of flanged rim 35 of the outer cannula 30 and connect the inner cannula 20 and outer cannula 30 together as shown in FIGS. 3–5 and 8. Interconnecting latching legs 26L and 26R project upwardly and inwardly from the hinged bridged regions 22B and 24B at a sufficiently outwardly distance for latching hooks 22H and 24H to hook and latch onto lip 35L of rim 35 of the outer cannula 30.

When the inner cannula 20 and outer cannula 30 are connected in this manner without the protective unlatching stop of this invention as shown in FIG. 4, the inner 20 and outer 30 cannula may be inadvertently separated from one another by disconnecting neck movement of the patient. When the patient P unwantedly disconnects the inner cannula 20 from the outer cannula 30, the inner cannula 20 remains connected to the vent tubing or elbow E which, in turn, fails to create sufficient back pressure to activate the ventilator's low pressure alarm circuitry which, in turn, if not corrected, can cause serious injury or death to the patient.

Figure 9:
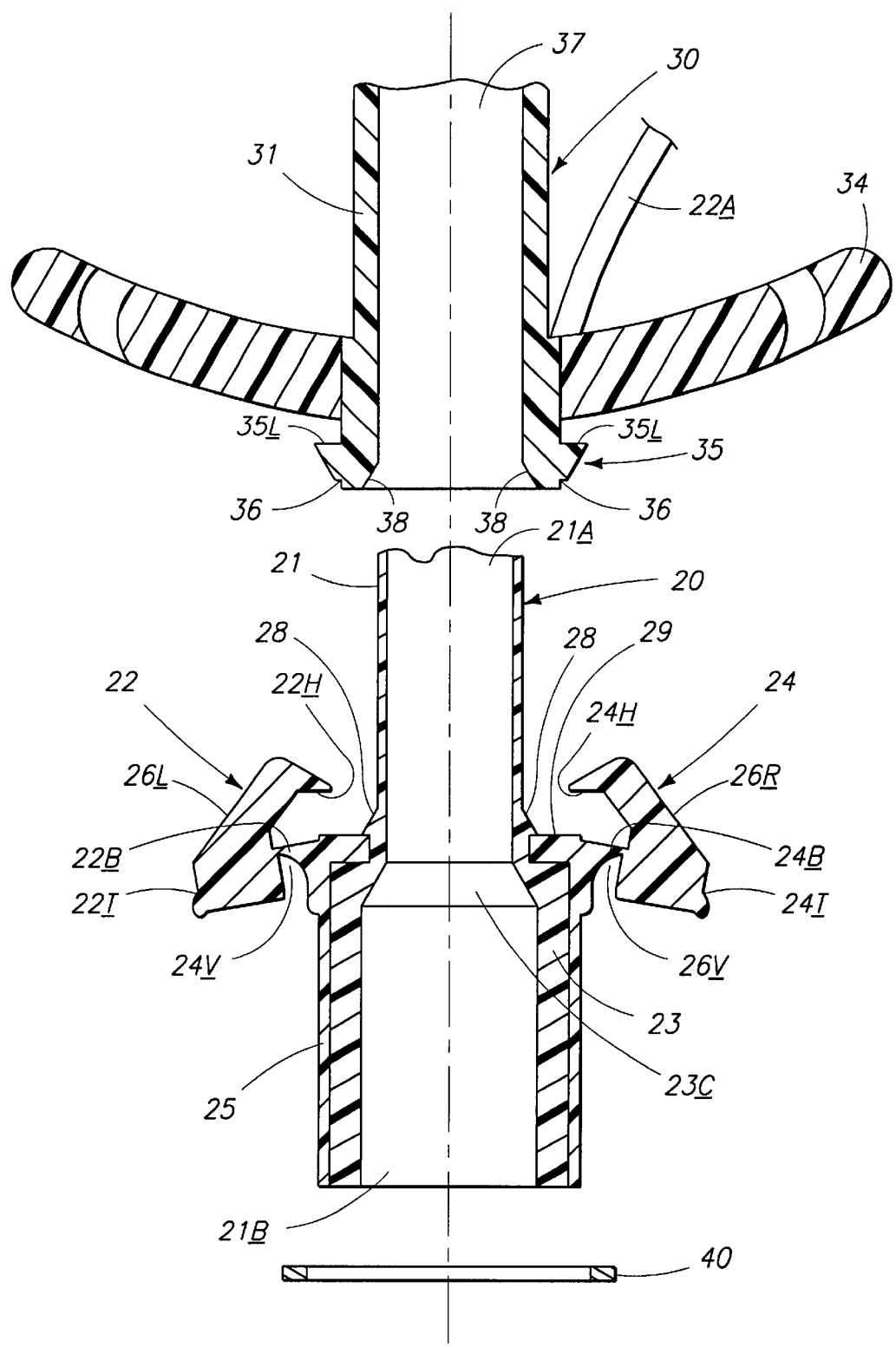
FIG. 9 is a partial cross-sectional view as shown in FIG. 8 with the inner cannula being shown as separated from the outer cannula

By inserting the interlocking stop 40 (e.g. in the form of a detachable annular ring such as a snap ring shown in FIGS. 6A, 6B, and 9) into the recesses of notched grooves 22V and 24V (as shown in FIGS. 1–3, 5 and 7–8), inadvertent or unwanted separation of the inner cannula 20 from the outer cannula 3 is prevented. As may be seen with reference to FIGS. 1–3, 5, and 7–8, the latching stop 40 biases the latching members 22 and 24 into a secure latching position, which requires an advertent removal of latching stop 40 in order to effectuate any separation of the inner cannula 20 from the outer cannula 30.

As may be observed in particular from FIGS. 1–3 and 8, the latching stop 40 prevents the latching tabs 22T and 24T of the inner cannula 20 from being depressed downwardly and inwardly towards the cylindrical base 25 which, in turn, unlatches the latching lips or hooks 22H and 24H of the latching members 24 of the inner cannula 20 from latching lip 35L of the flanged rim 35 of the outer cannula 30. Thus, as may be observed from the embodiments of the invention as disclosed, if the latching stop 40 is not removed from the tracheostomy device 1, inner cannula 20 cannot be dislodged from the outer cannula 30. Separation of the air supply can occur if connecting elbow E is removed from the interconnecting cylindrical base 25 passageway 21B which, in turn, creates a sufficiently low pressure so as to sound the low pressure alarming units within the hospital staffing or nursing unit. Unlike the conventional anti-disconnecting devices which cannot be separated at the connecting elbow causing tearing away of the inflated cuff and the whole tracheostomy assembly, separation occurs at the elbow E which also allows the alarm system to sound.

A rigid annular latching and seating member serves as a mounting site for mounting the inner cannula 20 onto the outer cannula 30 and an air line connecting site for connecting the air line to the tracheostomy device 1. The annular latching and seating member is laterally positioned inwardly from the terminating end of the cannula so as to provide a connecting site for mounting and latching the outer cannula 30 thereto. An inward beveled seat configured so as to matingly seal the corresponding flanged passageway seating site of the outer cannula provides an airtight seal when the outer cannula 30 and inner cannula 20 are coupled together.

What is claimed is:

1. In a tracheostomy device equipped with an outer cannula comprised of a tube open at both ends to provide passageway for gases and a transverse latching lip at a ventilating gas inlet end of the tube and an inner cannula comprised of a tubular section open to the flow of gas therethrough and a hallowed cylindrical base member having an external diameter greater than the tube, with said base member being open at a proximate end and equipped with an enclosing brim having a centrally disposed spouting aperture at a distal end of the base, a pair of hinged latches disposed about the outer peripheral margin of the brim and respectively connected to the brim by a pair of flexible bridges supportive of upwardly and inwardly disposed latching legs respectively terminated by latching hooks for latching onto latching lip of the outer cannula, a pair of unlatching tabs operatively connected to latching legs and extending downwardly and outwardly in an opposite direction from the latching legs, with said tabs being positioned in an unlatching position when depressed inwardly towards the base member to cause the latching hooks to unlatch brim from the latching lip, the improvement which comprises a detachable interlocking stop biasingly positioned in juxtaposition between the hinged latches and the base member so as to maintain the tabs in latched position and to prevent the tabs from being depressed to the unlatching positioned, thereby, retain interconnection of the outer cannula to the inner cannula in the latched position.

2. The improvement according to claim 1 wherein the interlocking stop comprises a detachable annular retaining ring slideably positioned and biased between the latching taps and hollowed cylindrical base member so as to maintain the tabs in the latched position.

3. The improvement according to claim 2 wherein the annular retaining ring comprises a snap ring.

4. A method for preventing unwanted separation of a tracheostomy device equipped with an outer cannula having an outer tube open at both ends to provide a passageway for gas and a transverse latching lip at ventilating gas inlet end of the tube and an inner cannula having an inner tubular section open to the flow of the gas therethrough concentrically positioned within the outer tube and a hollowed cylindrical base member having an external diameter greater than the outer tube extending outwardly from the inner tubular section, with said base member being open at a proximate end and equipped with an enclosing brim having a centrally disposed spouting aperture at a distal end of the base, a pair of hinged latches disposed about the outer peripheral margin of the brim and respectively connected to the brim by a pair of flexible bridges supportive of upwardly and inwardly disposed latching legs respectively terminated by latching hooks for latching onto latching lip of the outer cannula, a pair of unlatching tabs operatively connected to latching legs and extending downwardly and outwardly in an opposite direction from the latching legs, with said tabs being positioned in an unlatching position when depressed inwardly towards the base member as to cause the latching hooks to unlatch from the latching lip, said method comprising:

a) securing the tracheostomy device to a tracheostomy patient; and, b) emplacing a detached interlocking stop in a biasing juxtaposition between the unlatching tabs and the base member so as to maintain the tabs in a latched position and thereby prevent the tabs from being depressed to the unlatching position so as to retain interconnection of the outer cannula to position.

5. The method according to claim 4 which includes as additional steps of removing the interlocking stop from the device and separating the inner cannula from the outer cannula.

6. The method according to claim 5 wherein the emplacing comprises the emplacing of a snap ring as the annular retaining ring.

7. The method according to claim 4 wherein the interlocking stop comprises an annular retaining ring.

8. The method according to claim 7 wherein the annular retaining ring comprises a snap ring.

* * * * *